United States Patent
Candau et al.

(10) Patent No.: US 6,902,722 B2
(45) Date of Patent: *Jun. 7, 2005

(54) AQUEOUS ANTISUN/SUNSCREEN COMPOSITIONS COMPRISING AMPHIPHILIC 2-ACRYLAMIDOMETHYLPROPANESULFONIC ACID POLYMERS AND WATER-SOLUBLE SILICONES

(75) Inventors: Didier Candau, Bievres (FR); Karl Boutelet, Paris (FR); Nathalie Seyler, Maisons-Alfort (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/823,669

(22) Filed: Apr. 14, 2004

(65) Prior Publication Data

US 2004/0228814 A1 Nov. 18, 2004

Related U.S. Application Data

(60) Provisional application No. 60/468,053, filed on May 6, 2003.

(30) Foreign Application Priority Data

Apr. 14, 2003 (FR) .............................................. 03 04650

(51) Int. Cl.$^7$ .............................. A61K 7/42; A61K 7/44; A61K 7/00

(52) U.S. Cl. ........................... 424/59; 424/60; 424/400; 424/401

(58) Field of Search ........................... 424/59, 60, 400, 424/401

(56) References Cited

U.S. PATENT DOCUMENTS 5,338,352 A    8/1994   Breneman et al.

FOREIGN PATENT DOCUMENTS

EP        1 069 142 A1     1/2001
WO        WO 93/05762 A1   4/1993

OTHER PUBLICATIONS

French Search Report issued in French Priority Counterpart FR 03/04650 on Jan. 7, 2004, 2 pages.

Primary Examiner—Shelley A. Dodson
(74) Attorney, Agent, or Firm—Burns, Doane, Swecker & Mathis, L.L.P.

(57) ABSTRACT

Photoprotective compositions well suited for the photoprotection of the skin, lips and/or hair against the damaging effect of UV-radiation comprise at least one aqueous phase and at least one system for screening out UV-radiation, and which also contain:

(a) at least one partially or totally neutralized, crosslinked or non-crosslinked amphiphilic polymer of 2-acrylamidomethylpropanesulfonic acid (AMPS), and (b) at least one water-soluble silicone comprising at least one terminal or pendent monovalent polyoxyalkylene group.

38 Claims, No Drawings

AQUEOUS ANTISUN/SUNSCREEN COMPOSITIONS COMPRISING AMPHIPHILIC 2-ACRYLAMIDOMETHYLPROPANESULFONIC ACID POLYMERS AND WATER-SOLUBLE SILICONES

CROSS-REFERENCE TO PRIORITY/PROVISIONAL APPLICATIONS

This application claims priority under 35 U.S.C. § 119 of FR 03/04650, filed Apr. 14, 2003, and of provisional application Ser. No. 60/468,053, filed May 6, 2003, both hereby expressly incorporated by reference and both assigned to the assignee hereof. This application is also a continuation of said '053 provisional.

BACKGROUND OF THE INVENTION

1. Technical Field of the Invention

The present invention relates to photoprotective compositions comprising at least one aqueous phase and a system for screening out UV radiation, which comprise:

(a) at least one partially or totally neutralized, crosslinked or non-crosslinked amphiphilic polymer of 2-acrylamidomethylpropanesulfonic acid, and (b) at least one water-soluble silicone comprising at least one terminal or pendent monovalent polyoxyalkylene group.

This invention also relates to a combination of at least one partially or totally neutralized, crosslinked or non-crosslinked amphiphilic polymer of 2-acrylamidomethylpropanesulfonic acid and of at least one water-soluble silicone comprising at least one terminal or pendent monovalent polyoxyalkylene group, in an aqueous cosmetic composition comprising a photoprotective system capable of screening out UV radiation, to increase the sun protection factor.

2. Description of Background and/or Related and/or Prior Art

It is well known that light radiation with wavelengths of between 280 nm and 400 nm permits tanning of the human epidermis and that rays with wavelengths of between 280 nm and 320 nm, which are known as UV-B rays, cause skin burns and erythema that can harm the development of a natural tan; this UV-B radiation should thus be screened out.

It is also known that UV-A rays, with wavelengths of between 320 nm and 400 nm, which cause tanning of the skin, are liable to induce an impairment in the skin, especially in the case of sensitive skin or skin that is continually exposed to solar radiation. UV-A rays in particular bring about a loss of elasticity of the skin and the appearance of wrinkles, leading to premature aging. They promote the triggering of the erythmal reaction or amplify this reaction in certain individuals and may even be the cause of phototoxic or photoallergic reactions. It is thus desirable also to screen out UV-A radiation.

UV-A and UV-B rays should thus be screened out, and cosmetic compositions for protecting the human epidermis containing UV-A and UV-B-screening agents currently exist.

These antisun compositions are quite often in the form of an emulsion, of oil-in-water type (i.e., a cosmetically and/or dermatologically acceptable support consisting of an aqueous dispersing continuous phase and of a fatty dispersed discontinuous phase), or of water-in-oil type (aqueous phase dispersed in a continuous fatty phase), which contains, in varying concentrations, one or more standard liposoluble organic screening agents and/or standard water-soluble organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent. In such emulsions, the hydrophilic screening agents are present in the aqueous phase and the lipophilic screening agents are present in the fatty phase.

SUMMARY OF THE INVENTION

It has now surprisingly and unexpectedly been determined that by adding, to an aqueous support containing a system for screening out UV radiation, a partially or totally neutralized, crosslinked or non-crosslinked amphiphilic polymer of 2-acrylamidomethylpropanesulfonic acid and at least one water-soluble silicone comprising at least one terminal or pendent monovalent polyoxyalkylene group, aqueous antisun/sunscreen compositions are produced that have improved protection factors (SPFs), which are in all cases superior to those that may be obtained with such a photoprotective system alone.

In the remainder of the present description, the expression "system for screening out UV radiation" means an agent for screening out UV radiation comprising either a single organic or mineral compound for screening out UV radiation or a mixture of several organic or mineral compounds for screening out UV radiation, for example a mixture comprising a UV-A-screening agent and a UV-B-screening agent.

This discovery forms the basis of the present invention.

Thus, the present invention features photoprotective compositions comprising at least one aqueous phase and at least one system for screening out UV radiation, and which comprise:

(a) at least one partially or totally neutralized, crosslinked or non-crosslinked amphiphilic polymer of 2-acrylamidomethylpropanesulfonic acid (AMPS), and (b) at least one water-soluble silicone comprising at least one terminal or pendent monovalent polyoxyalkylene group.

This invention also features the combination of at least one partially or totally neutralized, crosslinked or non-crosslinked amphiphilic polymer of 2-acrylamidomethylpropanesulfonic acid and of at least one water-soluble silicone comprising at least one terminal or pendent monovalent polyoxyalkylene group, in an aqueous cosmetic composition comprising a photoprotective system capable of screening out UV radiation, to increase the sun protection factor.

Other characteristics, aspects and advantages of the invention will be seen from the detailed description that follows.

DETAILED DESCRIPTION OF BEST MODE AND SPECIFIC/PREFERRED EMBODIMENTS OF THE INVENTION

The AMPS polymers in accordance with the invention are amphiphilic, i.e., they comprise both a hydrophilic portion and a hydrophobic portion comprising at least one fatty chain.

For the purposes of the present invention, the term "fatty chain" means any hydrocarbon-based chain containing at least 7 carbon atoms.

The AMPS polymers in accordance with the invention are crosslinked or non-crosslinked homopolymers or copolymers comprising at least one 2-acrylamidomethylpropanesulfonic acid (AMPS) monomer, in free form or in partially or totally neutralized form.

Preferably, the AMPS polymers in accordance with the invention may be partially or totally neutralized with a mineral base (sodium hydroxide, potassium hydroxide or aqueous ammonia), an organic base such as monoethanolamine, diethanolamine or triethanolamine, an aminomethylpropanediol or N-methylglucamine, or basic amino acids, for instance arginine and lysine, and mixtures of these compounds. They are generally neutralized. In the present invention, the term "neutralized" refers to polymers that are totally or virtually totally neutralized, i.e., at least 90% neutralized.

These AMPS polymers according to the invention may be crosslinked or non-crosslinked.

When the polymers are crosslinked, the crosslinking agents may be selected from among the polyolefinically unsaturated compounds commonly used for crosslinking polymers obtained via free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

According to one preferred embodiment of the invention, the crosslinking agent is selected from among methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The fatty chain present in the polymers of the invention preferably contains from 7 to 30 carbon atoms, more preferably from 7 to 22 carbon atoms, even more preferably from 7 to 18 carbon atoms and more particularly from 12 to 18 carbon atoms.

The amphiphilic polymers in accordance with the invention generally have a weight-average molecular weight ranging from 50,000 to 10,000,000, more preferably from 100,000 to 8,000,000 and even more preferably from 100,000 to 7,000,000.

The amphiphilic AMPS polymers according to the invention may be crosslinked or non-crosslinked. The crosslinking agents may be selected from those mentioned above. Use will be made more particularly of methylenebisacrylamide, allyl methacrylate or trimethylolpropane triacrylate (TMPTA). The degree of crosslinking preferably ranges from 0.01 mol % to 10 mol % and more particularly from 0.2 mol % to 2 mol % relative to the polymer.

The amphiphilic AMPS polymers in accordance with the invention may be selected especially from random amphiphilic AMPS polymers modified by reaction with a $C_6$–$C_{22}$ n-monoalkylamine or di-n-alkylamine, such as those described in WO 00/31154. These polymers may also contain other ethylenically unsaturated hydrophilic monomers selected, for example, from among acrylic acid, methacrylic acid or the β-alkyl-substituted derivatives thereof or the esters thereof obtained with monoalkylene or polyalkylene glycols, acrylamide, methacrylamide, vinylpyrrolidone, itaconic acid or maleic acid, or mixtures thereof.

The preferred polymers of the invention are selected from among amphiphilic polymers of AMPS and of at least one ethylenically unsaturated monomer comprising at least one hydrophobic portion containing from 7 to 30 carbon atoms, more preferably from 7 to 22 carbon atoms, even more preferably from 7 to 18 carbon atoms and more particularly from 12 to 18 carbon atoms. This hydrophobic portion may be a saturated or unsaturated, linear (for example n-octyl, n-decyl, n-hexadecyl, n-dodecyl or oleyl), branched (for example isostearic) or cyclic (for example cyclododecane or adamantane) alkyl radical.

These same polymers may also contain one or more ethylenically unsaturated hydrophilic comonomers, for instance acrylic acid, methacrylic acid or the β-alkyl-substituted derivatives thereof or the esters thereof obtained with monoalkylene or polyalkylene glycols, acrylamide, methacrylamide, vinylpyrrolidone, itaconic acid or maleic acid.

These same polymers may also contain one or more ethylenically unsaturated hydrophobic comonomers comprising, for example:

a $C_7$–$C_{18}$ fluoro or alkylfluoro radical (for example the group of formula —$(CH_2)_2$—$(CF_2)_9$—$CF_3$), a cholesteryl radical or a cholesterol-based radical (for example cholesteryl hexanoate), an aromatic polycyclic group, for instance naphthalene or pyrene, a silicone, alkylsilicone or alkylfluorosilicone radical.

These copolymers are described especially in EP-A-750,899, U.S. Pat. No. 5,089,578 and in the following publications from Yotaro Morishima:

"Self-assembling amphiphilic polyelectrolytes and their nanostructures—Chinese Journal of Polymer Science, Vol. 18, No. 40, (2000), 323–336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694–3704";

"Solution properties of micelle networks formed by nonionic moieties covalently bound to a polyelectrolyte: salt effects on rheological behavior—Langmuir, 2000, Vol. 16, No. 12, 5324–5332";

"Stimuli responsive amphiphilic copolymers of sodium 2-(acrylamido)-2-methylpropanesulfonate and associative macromonomers—Polym. Preprint, Div. Polym. Chem., 1999, 40(2), 220–221".

They are also described in the (Clariant): EP-1,069,142, WO 02/44224, WO 02/44225, WO 02/44227, WO 02/44229, WO 02/44230, WO 02/44231, WO 02/44267, WO 02/44268, WO 02/44269, WO 02/44270, WO 02/44271, WO 02/43677, WO 02/43686, WO 02/43687, WO 02/43688, WO 02/43689.

The ethylenically unsaturated hydrophobic monomers of the invention are preferably selected from among the acrylates or acrylamides of formula (1) below:

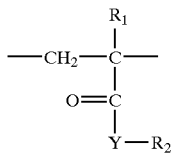

(1)

in which $R_1$ is a hydrogen atom or a linear or branched $C_1$–$C_6$ alkyl radical (preferably methyl); Y is O or NH; and $R_2$ is a hydrophobic radical comprising a fatty chain containing from 7 to 22 carbon atoms, preferably from 7 to 18 and more particularly from 12 to 18 carbon atoms.

The hydrophobic radical $R_2$ is preferably selected from among saturated or unsaturated linear $C_7$–$C_{18}$ alkyl radicals (for example n-octyl, n-decyl, n-hexadecyl, n-dodecyl or oleyl), branched alkyl radicals (for example isostearic) or cyclic alkyl radicals (for example cyclododecane or adamantane), $C_7$–$C_{18}$ alkylperfluoro radicals (for example the group of formula —$(CH_2)_2$—$(CF_2)_9$—$CF_3$), the cholesteryl radical or a cholesterol ester, for instance cholesteryl hexanoate, aromatic polycyclic groups, for instance naphthalene or pyrene. Among these radicals, linear and branched alkyl radicals are more particularly preferred.

According to one particularly preferred embodiment of the invention, the hydrophobic radical $R_2$ also comprises at least one alkylene oxide unit and preferably a polyoxyalkylene chain. The polyoxyalkylene chain preferably comprises ethylene oxide units and/or propylene oxide units and even more particularly solely comprises ethylene oxide units. The number of moles of oxyalkylene units generally ranges from 1 to 30 mol, more preferably from 1 to 25 mol and even more preferably from 3 to 20 mol.

Among these polymers that may be mentioned are:

crosslinked or non-crosslinked, neutralized or non-neutralized copolymers comprising from 15% to 60% by weight of AMPS units and from 40% to 85% by weight of ($C_8$–$C_{16}$)alkyl(meth)acrylamide units or of ($C_8$–$C_{16}$)alkyl (meth)acrylate units relative to the polymer, such as those described in EP-A-750,899;

terpolymers comprising from 10 mol % to 90% of acrylamide units, from 0.1 mol % to 10 mol % of AMPS units and from 5 mol % to 80 mol % of n-($C_6$–$C_{18}$) alkylacrylamide units relative to the polymer, such as those described in U.S. Pat. No. 5,089,578.

Amphiphilic polymers that may also be mentioned include copolymers of totally neutralized AMPS and of n-dodecyl, n-hexadecyl and/or n-octadecyl methacrylate, and also non-crosslinked and crosslinked copolymers of AMPS and of n-dodecylmethacrylamide, such as those described in the Morishima articles mentioned above.

Mention will be made more particularly of crosslinked or non-crosslinked amphiphilic copolymers comprising:

(a) 2-acrylamido-2-methylpropanesulfonic acid (AMPS) units of formula (2) below:

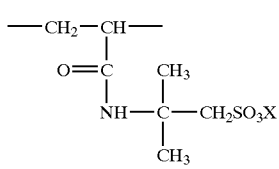

(2)

in which $X^+$ is a proton, an alkali metal cation, an alkaline-earth metal cation or an ammonium ion;

(b) and units of formula (3) below:

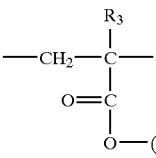

(3)

in which n and p, which may be identical or different, denote a number of moles and range from 0 to 30, preferably from 1 to 25 and more preferably from 3 to 20, with the proviso that n+p is less than or equal to 30, preferably less than 25 and better still less than 20; $R_3$ is a hydrogen atom or a linear or branched $C_1$–$C_6$ alkyl radical (preferably methyl); $R_4$ is a linear or branched alkyl comprising m carbon atoms ranging from 7 to 22, preferably from 7 to 18 carbon atoms and better still from 12 to 18 carbon atoms.

In formula (2), the cation $X^+$ more particularly is sodium or ammonium.

Among the monomers of formula (3) that may be mentioned are:

esters of (meth)acrylic acid and of a $C_{10}$–$C_{18}$ fatty alcohol polyoxyethylenated with 8 EO, for instance the product Genapol C-080 sold by Clariant, esters of (meth)acrylic acid and of a $C_{11}$ fatty oxo alcohol polyoxyethylenated with 8 EO, for instance the product Genapol UD-080 sold by Clariant, esters of (meth)acrylic acid and of a $C_{12}$–$C_{14}$ polyoxyethylenated fatty alcohol with 7 EO, for instance the product Genapol LA-070 sold by Clariant, esters of (meth)acrylic acid and of a $C_{12}$–$C_{14}$ polyoxyethylenated fatty alcohol with 11 EO, for instance the product Genapol LA-110 sold by Clariant, esters of (meth)acrylic acid and of a $C_{16}$–$C_{18}$ polyoxyethylenated fatty alcohol with 8 EO, for instance the product Genapol T-080 sold by Clariant, esters of (meth)acrylic acid and of a $C_{16}$–$C_{18}$ polyoxyethylenated fatty alcohol with 15 EO, for instance the product Genapol T-150 sold by Clariant, esters of (meth)acrylic acid and of a $C_{16}$–$C_{18}$ polyoxyethylenated fatty alcohol with 11 EO, for instance the product Genapol T-110 sold by Clariant, esters of (meth)acrylic acid and of a $C_{16}$–$C_{18}$ polyoxyethylenated fatty alcohol with 20 EO, for instance the product Genapol T-200 sold by Clariant, esters of (meth)acrylic acid and of a $C_{16}$–$C_{18}$ polyoxyethylenated fatty alcohol with 25 EO, for instance the product Genapol T-250 sold by Clariant, esters of (meth)acrylic acid and of a $C_{18}$–$C_{22}$ polyoxyethylenated fatty alcohol with 25 EO and/or of a $C_{16}$–$C_{18}$ polyoxyethylenated fatty isoalcohol with 25 EO.

The products that will be selected more particularly are:

(i) non-crosslinked products for which p=0, n=7 or 25, $R_3$ is methyl and $R_4$ is a $C_{12}$–$C_{14}$ or $C_{16}$–$C_{18}$ alkyl mixture, (ii) crosslinked products for which p=0, n=8 or 25, $R_3$ is methyl and $R_4$ is a $C_{16}$–$C_{18}$ alkyl mixture.

These polymers are described and synthesized in EP-1, 069,142. These particular amphiphilic polymers may be obtained according to the standard processes of free-radical polymerization in the presence of one or more initiators, for instance azobisisobutyronitrile (AIBN), azobisdimethylvaleronitrile, 2,2-azobis(2-amidinopropane) hydrochloride (ABAH), organic peroxides such as dilauryl peroxide, benzoyl peroxide, tert-butyl hydroperoxide, etc., mineral peroxide compounds such as potassium or ammonium persulfate, or $H_2O_2$ optionally in the presence of reducing agents.

These amphiphilic polymers may be obtained especially by free-radical polymerization in tert-butanol medium, in which they precipitate. By using precipitation polymerization in tert-butanol, it is possible to obtain a size distribution of the polymer particles that is particularly favourable for its uses.

The reaction may be performed at a temperature of between 0 and 150° C. and preferably between 10 and 100° C., either at atmospheric pressure or under reduced pressure. It may also be performed under inert atmosphere and preferably under nitrogen.

The polymers in accordance with the invention are preferably partially or totally neutralized with a mineral or organic base, such as those mentioned above.

The molar percentage concentration of the units of formula (2) and of the units of formula (3) in the amphiphilic polymers according to the invention varies as a function of the desired cosmetic application, the nature of the emulsion (oil-in-water or water-in-oil emulsion) and the Theological properties of the desired formulation. It can range between 0.1 and 99.9 mol %.

The amphiphilic AMPS polymers according to the invention, which are sparingly hydrophobic, will be more suitable for thickening and/or stabilizing oil-in-water emulsions. The molar proportion of units of formula (3) will preferably range from 0.1% to 50%, more particularly from 1% to 25% and even more particularly from 3% to 10%.

The amphiphilic AMPS polymers according to the invention that are more hydrophobic will be more suitable for thickening and/or stabilizing water-in-oil emulsions. The molar proportion of units of formula (3) will preferably range from 50.1% to 99.9%, more particularly from 60% to 95% and even more particularly from 65% to 90%.

The distribution of the monomers in the polymers of the invention may be, for example, alternate, block (including multiblock) or random.

The AMPS polymers in accordance with the invention are generally present in active-material amounts ranging from 0.01% to 20% by weight, more preferably from 0.1% to 10% by weight, even more preferably from 0.1% to 5% by weight and even more particularly from 0.5% to 2% by weight relative to the total weight of the composition.

The silicones comprising at least one terminal or pendent monovalent polyoxyalkylene group that may be used according to the invention are water-soluble. This means that, at a concentration of 0.2% by weight at 25° C. in water, they form a macroscopically homogeneous solution.

The water-soluble silicones of the invention are preferably selected from among the compounds of general formulae (I) and (II):

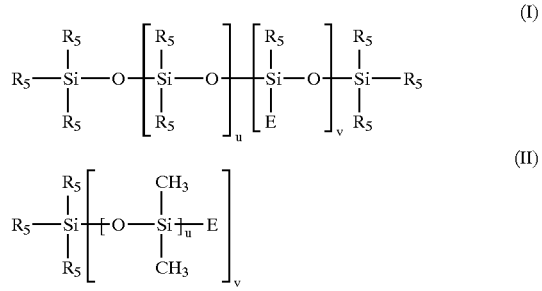

in which the radicals $R_5$, which may be identical or different, are each a monovalent hydrocarbon-based radical selected from alkyl, aryl and aralkyl radicals containing not more than 10 carbon atoms and preferably selected from among $C_1$–$C_4$ lower alkyl radicals, for instance methyl, ethyl or butyl, or selected from phenyl and benzyl, and even more preferably all are methyl; some of the radicals $R_5$ may also additionally contain an ethylcyclohexylene monoxide group and are in small proportion in the polysiloxane chain;

u ranges from 10 to 150, preferably from 25 to 100 and more preferably from 65 to 85;

v ranges from 3 to 12, preferably from 4 to 10 and more preferably from 5 to 8;

E is a group $-C_xH_{2x}-(OC_2H_4)_y-(OC_3H_6)_z-OR_6$ in which x ranges from 1 to 8, preferably from 2 to 4 and more preferably 3;

y>0 and z≧0; y and z are selected such that the total molecular weight of the radical E ranges from 200 to 10,000 and more preferably from 350 to 4,000; and $R_6$ is hydrogen, a linear or branched $C_1$–$C_8$ alkyl radical (preferably a $C_1$–$C_4$ radical, for instance methyl), a $C_2$–$C_8$ acyl radical (preferably a $C_2$–$C_4$ radical, for instance acetyl).

In formula E, when z is positive, the oxyethylene and oxypropylene units may be randomly distributed in the polyether chain E and/or may be in the form of blocks.

The water-soluble silicones in accordance with the invention are known and described especially in U.S. Pat. No. 5,338,352, and the method for preparing them is described especially in U.S. Pat. No. 4,847,398.

Such silicones are sold, for example, by OSI under the trademarks Silwet L-720®, Silwet L-7002®, Silwet L-7600®, Silwet L-7604®, Silwet L-7605®, Silwet L-7607®, Silwet L-7657®, Silwet L-7200® and Silwet L7230®.

According to the invention, the water-soluble silicone(s) modified with oxyalkylene groups can represent from 0.01% to 20% by weight, preferably from 0.1% to 15% by weight and more particularly from 0.5% to 5% by weight relative to the total weight of the final composition.

The compositions according to the invention may be in any galenical form comprising an aqueous phase conventionally used for topical application, and especially compositions free of a fatty phase, for instance lotions or sera, or aqueous gels; compositions comprising at least one fatty phase, for instance emulsions of liquid or semi-liquid consistency of the milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O emulsions), microemulsions, vesicular dispersions of ionic and/or nonionic type, or wax/aqueous phase dispersions. These compositions are prepared according to the usual methods.

According to one particular embodiment of the invention, the oil-in-water or water-in-oil emulsions prepared with the amphiphilic AMPS polymers and the water-soluble polyoxyalkylene silicones according to the invention may comprise only 1% by weight or less, and may even be free of emulsifying surfactants, while at the same time being stable on storage.

The nature of the fatty phase forming part of the composition of the emulsions according to the invention is not critical, and it may thus consist of any compound already known in general as being suitable for the manufacture of emulsions of water-in-oil type. In particular, these compounds may be selected, alone or as mixtures, from various fatty substances, oils of plant, animal or mineral origin, natural or synthetic waxes, and the like.

Among the oils that can form part of the composition of the fatty phase, mention may be made especially of:

mineral oils such as liquid paraffin and liquid petroleum jelly, oils of animal origin such as perhydrosqualene, oils of plant origin such as sweet almond oil, avocado oil, castor oil, olive oil, jojoba oil, sesame seed oil, groundnut oil, grapeseed oil, rapeseed oil, coconut oil, hazelnut oil, shea butter, palm oil, apricot kernel oil, beauty-leaf oil, rice bran oil, maize germ oil, wheatgerm oil, soybean oil, sunflower oil, evening primrose oil, safflower oil, passionflower oil and rye oil, synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate and isocetyl lanolate, isoparaffins and poly-α-olefins.

As other oils that may be used in the emulsions according to the invention, mention may also be made of $C_{12}$–$C_{15}$ fatty alkyl benzoates (Finsolv TN from Finetex), fatty alcohols such as lauryl alcohol, cetyl alcohol, myristyl alcohol, stearyl alcohol, palmityl alcohol, oleyl alcohol and 2-octyldodecanol, acetyl glycerides, octanoates and decanoates of alcohols and of polyalcohols, such as those of glycol and of glycerol, ricinoleates of alcohols and of polyalcohols such as cetyl ricinoleate, fatty acid triglycerides such as caprylic/capric triglycerides, triglycerides of $C_{10}$–$C_{18}$ saturated fatty acids, fluoro oils, perfluoro oils, lanolin, hydrogenated lanolin, acetylated lanolin and, finally, volatile or non-volatile silicone oils.

Needless to say, the fatty phase may also contain one or more standard lipophilic cosmetic adjuvants, especially those that are already usually used in the manufacture and production of antisun cosmetic compositions.

The dispersing aqueous phase may conventionally comprise water or a mixture of water and polyhydric alcohol(s), for instance glycerol, propylene glycol and sorbitol, or alternatively a mixture of water and of water-soluble lower alcohol(s) such as ethanol, isopropanol or butanol (aqueous-alcoholic solution), and it can, of course, also contain standard water-soluble cosmetic adjuvants.

The compositions in accordance with the invention comprise a system for screening out UV radiation, which may comprise one or more UV-A-active and/or UV-B-active organic or mineral UV-screening agents, which are water-soluble or liposoluble, or even insoluble in the cosmetic solvents commonly used.

The additional organic screening agents are selected especially from among anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469, EP-933,376, EP-507,691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; benzoxazole derivatives as described in EP-0,832,642, EP-1,027,883, EP-1,300,137 and DE-101-62-844; methylenebis(hydroxyphenylbenzotriazole) derivatives as described in U.S. Pat. Nos. 5,237,071, 5,166,355, GB-2-303-549, DE-197-26-184 and EP-893,119; screening polymers and screening silicones such as those described especially in WO 93/04665; dimers derived from α-alkylstyrene, such as those described in DE-198-55-649; 4,4-diarylbutadienes such as those described in DE-197-55-649, EP-916,335, EP-1,133,980 and EP-1,133,981 and EP-A-1,008,586, and mixtures thereof.

As examples of UV-A-active and UV-B-active organic screening agents, mention may be made of those denoted hereinbelow under their INCI name:

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.
Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.
Dibenzoylmethane Derivatives:
Butyl methoxydibenzoylmethane sold in particular under the trademark "Parsol 1789" by Hoffmann LaRoche,
Isopropyldibenzoylmethane.
Cinnamic Derivatives:
Ethylhexyl methoxycinnamate sold in particular under the trademark "Parsol MCX" by Hoffmann LaRoche,
Isopropyl methoxycinnamate,
Isoamyl methoxycinnamate sold under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.
β,β-Diphenylacrylate Derivatives:
Octocrylene sold in particular under the trademark "Uvinul N539" by BASF,
Etocrylene sold in particular under the trademark "Uvinul N35" by BASF.
Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12,
n-Hexyl 2-(4-diethylamino-2-hydroxybenzoyl)benzoate.
Benzylidenecamphor Derivatives:
3-Benzylidenecamphor manufactured under the name "Mexoryl SD" by Chimex,
4-Methylbenzylidenecamphor sold under the name "Eusolex 6300" by Merck, Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.
Benzimidazole Derivatives:
Phenylbenzimidazolesulfonic acid sold in particular under the trademark "Eusolex 232" by Merck,
Disodium phenyl dibenzimidazole tetrasulfonate sold under the trademark "Neo Heliopan AP" by Haarmann and Reimer.
Triazine Derivatives:
Anisotriazine sold under the trademark "Tinosorb S" by Ciba Specialty Chemicals,
Ethylhexyltriazone sold in particular under the trademark "Uvinul T150" by BASF,
Diethylhexylbutamidotriazone sold under the trademark "Uvasorb HEB" by Sigma 3V.
2,4,6-Tris(diisobutyl 4'-aminobenzalmalonate)-s-triazine.
Benzotriazole Derivatives:
Drometrizole trisiloxane sold under the name "Silatrizole" by Rhodia Chimie,
Methylenebis(benzotriazolyl)tetramethylbutylphenol sold in solid form under the trademark "Mixxim BB/100" by Fairmount Chemical, or in micronized form as an aqueous dispersion under the trademark "Tinosorb M" by Ciba Specialty Chemicals.
Anthranilic Derivatives:
Menthyl anthranilate sold under the trademark "Neo Heliopan MA" by Haarmann and Reimer.
Imidazoline Derivatives:
Ethylhexyldimethoxybenzylidenedioxoimidazoline propionate.
Benzalmalonate Derivatives:
Polyorganosiloxane containing benzalmalonate functions, such as the product Polysilicone-15 sold under the trademark "Parsol SLX" by Hoffmann LaRoche
4,4-Diarylbutadiene Derivatives:
1,1-Dicarboxy(2,2'-dimethylpropyl)-4,4-diphenylbutadiene.
Benzoxazole Derivatives:
2,4-Bis[5-1(dimethylpropyl)benzoxazol-2-yl(4-phenyl)imino]-6-(2-ethylhexyl)imino-1,3,5-triazine sold under the name Uvasorb K2A by Sigma 3V,
and mixtures thereof.

The organic screening agents that are more particularly preferred are selected from among the following compounds:
Ethylhexyl salicylate,
Ethylhexyl methoxycinnamate,
Octocrylene,
Butyl methoxydibenzoylmethane,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyldibenzimidazoletetrasulfonate,
2,4,6-Tris(diisobutyl 4'-aminobenzalmalonate)-s-triazine,
Anisotriazine,
Ethylhexyltriazone,
Diethylhexylbutamidotriazone,
Methylenebis(benzotriazolyl)tetramethylbutylphenol,
Drometrizole trisiloxane,
Polysilicone-15,
1,1-Dicarboxy(2',2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine
and mixtures thereof.

The mineral screening agents are selected from among pigments or even nanopigments (mean size of the primary particles: generally between 5 nm and 100 nm and preferably between 10 nm and 50 nm) of coated or uncoated metal oxides such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminium stearate. Such coated or uncoated metal oxide nanopigments are described in particular in EP-518,772 and EP-518,773.

The screening system according to the invention is generally present in the compositions according to the invention in a content ranging from 0.1% to 30% by weight and preferably from 0.5% to 15% by weight relative to the total weight of the composition.

The compositions according to the invention may also contain agents for artificially tanning and/or browning the skin (self-tanning agents).

The self-tanning agents are generally selected from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in FR-2,466,492 and WO 97/35842, dihydroxyacetone (DHA) and 4,4-dihydroxypyrazolin-5-one derivatives as described in EP-903,342. DHA will preferably be used.

The DHA may be used in free form and/or in encapsulated form, for example in lipid vesicles such as liposomes, described especially in WO 97/25970.

The monocarbonyl or polycarbonyl self-tanning agents are generally present in the compositions according to the invention in proportions ranging from 0.1% to 10% by weight relative to the total weight of the composition and preferably from 0.2% to 8% by weight relative to the total weight of the composition.

The compositions in accordance with the present invention may also comprise standard cosmetic adjuvants selected especially from organic solvents, ionic or nonionic thickeners, softeners, humectants, opacifiers, stabilizers, emollients, silicones, insect repellents, fragrances, preserving agents, surfactants, fillers, active agents, pigments, polymers, propellants, acidifying or basifying agents or any other ingredient usually used in cosmetics and/or dermatology.

Needless to say, one skilled in this art will take care to select the optional additional compound(s) mentioned above and/or the amounts thereof such that the advantageous properties intrinsically associated with the compositions in accordance with the invention are not, or are not substantially, adversely affected by the envisaged addition(s).

Among the organic solvents that may be mentioned are lower alcohols and polyols.

Among the thickeners that may be mentioned are crosslinked acrylic polymers, for instance the Carbomer products sold by Noveon, acrylate/$C_{10}$–$C_{30}$ alkylacrylate crosslinked polymers of the Pemulen type sold by Noveon or Polyacrylate-3 sold under the name Viscophobe DB 1000 by Amerchol; polymers derived from 2-acrylamidomethylpropanesulfonic acid (Hostacerin AMPS sold by Clariant, or Sepigel 305 sold by SEPPIC), synthetic neutral polymers such as poly-N-vinylpyrrolidone, polysaccharides, for instance modified or unmodified guar gums, xanthan gums and cellulose derivatives, for instance hydroxypropyl guar gum, methylhydroxyethylcellulose and hydroxypropylmethylcellulose.

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

The present invention thus features the use of the compositions according to the invention as defined above for the manufacture of products for the cosmetic treatment of the skin, the lips and the hair, including the scalp, especially for protecting and/or caring for the skin, the lips and/or the hair, and/or for making up the skin and/or the lips.

The cosmetic compositions according to the invention may be used, for example, as care products and/or antisun/sunscreen products for the face and/or the body, of liquid to semi-liquid consistency, such as milks, more or less rich creams, cream-gels and pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

The following formulations were prepared and compared:

Formulation A: Cosmetic support containing a photoprotective system and a crosslinked copolymer of acrylamido-2-methyl-2-propanesulfonic acid (AMPS) and of a hydrophobic monomer derived from an ethoxylated fatty alcohol.

Formulation B: A cosmetic support containing a photoprotective system and a crosslinked or non-crosslinked copolymer of acrylamido-2-methyl-2-propanesulfonic acid and of a hydrophobic monomer derived from an ethoxylated fatty alcohol combined with a water-soluble oxyalkylenated polydimethylsiloxane.

| Compositions tested | A (outside the invention) | B (invention) |
|---|---|---|
| Octocrylene (Uvinul N 539 from BASF) | 9 | 9 |
| Butylmethoxydibenzoylmethane (Parsol 1789 from Hoffman LaRoche | 2.5 g | 2.5 g |
| Drometrizole trisiloxane (Silatrizole from Rhodia) | 0.75 g | 0.75 g |
| $C_{12}/C_{15}$ alkyl benzoate | 6 g | 6 g |
| Crosslinked copolymer of AMPS and of a (meth)acrylic acid ester of a $C_{16}$–$C_{18}$ fatty alcohol polyoxyethylenated with 25 EO (Genapol T-250) such as the product described in Example 3 of EP-1,059,142 | 1.25 g | 1.25 g |
| Glycerol | 4 g | 4 g |
| Propylene glycol | 4 g | 4 g |
| Terephthalylidenedicamphor-sulfonic acid (Mexoryl SX from Chimex) | 1.5 g | 1.5 g |
| Anatase titanium oxide (60 nm) coated with silica/alumina, as a protected aqueous dispersion | 16.7 g | 16.7 g |
| Water-soluble oxyalkylenated PDMS (Silwet L-7657 ® from OSI) |  | 1 g |
| Ethylenediaminetetraacetic acid, disodium salt | Qs | qs |
| Preserving agents | Qs | qs |
| Water | 53.2 g | 52.2 g |

For each of the formulations A and B, the sun protection factor (SPF) was then determined in vivo.

The sun protection factor was measured according to the following method: these formulations were applied, at a rate of 2 mg of product/cm² of skin, to the back of five human models, and the protected areas and non-protected areas of skin were then simultaneously subjected to the action of a sun simulator sold under the name "Xenon Multiport WG 320-UG 11"; the sun protection (SPF) was then calculated mathematically by the ratio of the irradiation time that was required to reach the erythema-forming threshold with formulation A or B (protected area) to the time required to reach the erythema-forming threshold without the formulation (unprotected area).

|  | Formulation A (outside the invention) | Formulation B (invention) |
|---|---|---|
| in vivo SPF | 16.5 ± 3.8 | 23 ± 3.9 |

It is noted that a photoprotective composition based on a crosslinked or non-crosslinked copolymer of acrylamido-2-methyl-2-propanesulfonic acid and of a hydrophobic monomer derived from an ethoxylated fatty alcohol combined with a water-soluble oxyalkylenated polydimethylsiloxane allows the sun protection factor to be increased by 28%.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective composition comprising at least one aqueous phase and at least one system for screening out UV-radiation, further comprising:
   (a) at least one partially or totally neutralized, crosslinked or non-crosslinked amphiphilic polymer of 2-acrylamidomethylpropanesulfonic acid (AMPS), and
   (b) at least one water-soluble silicone comprising at least one terminal or pendent monovalent polyoxyalkylene group.

2. The photoprotective composition as defined by claim 1, said at least one AMPS polymer being partially or totally neutralized with a mineral or organic base.

3. The photoprotective composition as defined by claim 2, such neutralization being with sodium hydroxide, potassium hydroxide or aqueous ammonia.

4. The photoprotective composition as defined by claim 2, such neutralization being with monoethanolamine, diethanolamine, triethanolamine, aminomethylpropanediol, n-methylglucamine, basic amino acids, and mixtures thereof.

5. The photoprotective composition as defined by claim 1, said at least one AMPS polymer being at least 90% neutralized.

6. The photoprotective composition as defined by claim 1, said at least one AMPS polymer being crosslinked with polyolefinically unsaturated compounds.

7. The photoprotective composition as defined by claim 6, the crosslinking agent being selected from among divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures thereof.

8. The photoprotective composition as defined by claim 5, the crosslinking agent being selected from among methylenebisacrylamide, allyl methacrylate and trimethylolpropane triacrylate (TMPTA).

9. The photoprotective composition as defined by claim 6, the degree of crosslinking ranging from 0.01 mol % to 10 mol % relative to the polymer.

10. The photoprotective composition as defined by claim 1, said at least one amphiphilic AMPS polymer comprising at least one fatty chain containing from 7 to 30 carbon atoms.

11. The photoprotective composition as defined by claim 1, said at least one amphiphilic AMPS polymer having a weight-average molecular weight ranging from 50,000 to 10,000,000.

12. The photoprotective composition as defined by claim 1, said at least one amphiphilic AMPS polymer comprising a random amphiphilic polymer of AMPS modified by reaction with a $C_6$–$C_{22}$ n-monoalkylamine or di-n-alkylamine, optionally comprising the polymerizate of one or more ethylenically unsaturated hydrophilic monomers.

13. The photoprotective composition as defined by claim 1, said at least one amphiphilic AMPS polymer comprising a polymer of AMPS and of at least one ethylenically unsaturated monomer which comprises at least one hydrophobic moiety containing from 7 to 30 carbon atoms, and optionally one or more ethylenically unsaturated hydrophilic comonomers.

14. The photoprotective composition as defined by claim 13, in which the ethylenically unsaturated monomers comprising at least one hydrophobic moiety containing from 7 to 30 carbon atoms are selected from among the acrylates or acrylamides of formula (1) below:

in which $R_1$ is a hydrogen atom or a linear or branched $C_1$–$C_6$ alkyl radical; Y is O or NH; and $R_2$ is a hydrophobic radical comprising a fatty chain containing from 7 to 22 carbon atoms.

15. The photoprotective composition as defined by claim 14, in which the hydrophobic radical $R_2$ is selected from among linear or branched, saturated or unsaturated $C_7$–$C_{18}$ alkyl radicals, $C_7$–$C_{18}$ alkylperfluoro radicals, the cholesteryl radical or a cholesterol ester, and aromatic polycyclic groups.

16. The photoprotective composition as defined by claim 14, in which the hydrophobic radical $R_2$ also comprises at least one alkylene oxide structural unit.

17. The photoprotective composition as defined by claim 16, in which the number of moles of oxyalkylene units ranges from 1 to 30 mol.

18. The photoprotective composition as defined by claim 14, in which the amphiphilic AMPS polymers are amphiphilic copolymers of:
   (a) 2-acrylamido-2-methylpropanesulfonic acid (AMPS) structural units of formula (2) below:

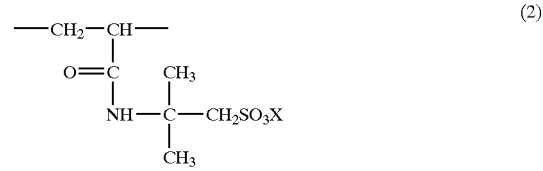

in which $X^+$ is a proton, an alkali metal cation, an alkaline earth metal cation or an ammonium ion; and
   (b) structural units of formula (3) below:

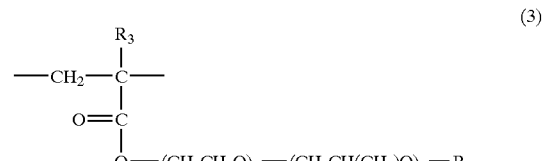

in which n and p, independently of one another, denote a number of moles and range from 0 to 30, with the proviso that n+p is less than or equal to 30; $R^3$ is a hydrogen atom or a linear or branched $C_1$–$C_6$ alkyl radical and $R_4$ is a linear or branched alkyl radical comprising m carbon atoms ranging from 7 to 22.

19. The photoprotective composition as defined by claim 18, in which $X^+$ is sodium or ammonium.

20. The photoprotective composition as defined by claim 17, in which the structural unit of formula (3) is selected from among:

esters of (meth)acrylic acid and of a $C_{10}$–$C_{18}$ fatty alcohol polyoxyethylenated with 8 EO, esters of (meth)acrylic acid and of a $C_{11}$ fatty oxo alcohol polyoxyethylenated with 8 EO, esters of (meth)acrylic acid and of a $C_{12}$–$C_{14}$ polyoxyethylenated fatty alcohol with 7 EO, esters of (meth)acrylic acid and of a $C_{12}$–$C_{14}$ polyoxyethylenated fatty alcohol with 11 EO, esters of (meth)acrylic acid and of a $C_{16}$–$C_{18}$ polyoxyethylenated fatty alcohol with 8 EO, esters of (meth)acrylic acid and of a $C_{16}$–$C_{18}$ polyoxyethylenated fatty alcohol with 15 EO, esters of (meth)acrylic acid and of a $C_{16}$–$C_{18}$ polyoxyethylenated fatty alcohol with 11 EO, esters of (meth)acrylic acid and of a $C_{16}$–$C_{18}$ polyoxyethylenated fatty alcohol with 20 EO, esters of (meth)acrylic acid and of a $C_{16}$–$C_{18}$ polyoxyethylenated fatty alcohol with 25 EO, and esters of (meth)acrylic acid and of a $C_{18}$–$C_{22}$ polyoxyethylenated fatty alcohol with 25 EO and/or of a $C_{16}$–$C_{18}$ polyoxyethylenated fatty isoalcohol with 25 EO.

21. The photoprotective composition as defined by claim 18, in which the amphiphilic AMPS polymers are selected from among:

(i) non-crosslinked products for which p=0, n=7 or 25, $R_3$ is methyl and $R_4$ is a $C_{12}$–$C_{14}$ or $C_{16}$–$C_{18}$ alkyl mixture, (ii) crosslinked products for which p=0, n=8 or 25, $R_3$ is methyl and $R_4$ is a $C_{16}$–$C_{18}$ alkyl mixture.

22. The photoprotective composition as defined by claim 18, in which the molar proportion of structural units of formula (3) ranges from 0.1% to 50%.

23. The photoprotective composition as defined by claim 18, in which the molar proportion of structural units of formula (3) ranges from 50.1% to 99.9%.

24. The photoprotective composition as defined by claim 1, in which the AMPS polymers are present in active material amounts ranging from 0.01% to 20% by weight relative to the total weight of the composition.

25. The photoprotective composition as defined by claim 1, said at least one water-soluble silicone comprising at least one terminal or pendent monovalent polyoxyalkylene group being selected from among the compounds of general formulae (I) and (II) below:

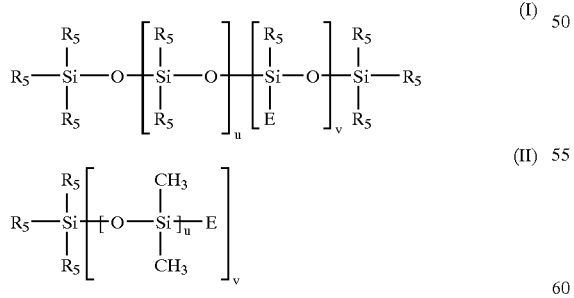

in which the radicals $R_5$, which may be identical or different, are each a monovalent hydrocarbon-based radical selected from among alkyl, aryl and aralkyl groups containing not more than 10 carbon atoms; a fraction of the radicals $R_5$ optionally containing an ethylcyclohexylene monoxide group;

u ranges from 10 to 150;

v ranges from 3 to 12;

E is a group $—C_xH_{2x}—(OC_2H_4)_y—(OC_3H_6)_z—OR_6$ in which x ranges from 1 to 8; y>0 and z≧0; y and z being selected such that the total molecular weight of the radical E ranges from 200 to 10 000; and $R_6$ is hydrogen, a linear or branched $C_1$–$C_8$ alkyl radical, a linear or branched $C_2$–$C_8$ acyl radical.

26. The photoprotective composition as defined by claim 25, in which the radicals $R_5$ are $C_1$–$C_4$ lower alkyl radical; $R_6$ is hydrogen, a $C_1$–$C_4$ alkyl radical or a $C_2$–$C_4$ acyl radical; x ranges from 2 to 4 and y and z are selected such that the total molecular weight of the radical E ranges from 350 to 4,000.

27. The photoprotective composition as defined by claim 26, in which all of the radicals $R_5$ are methyl; $R_6$ is hydrogen, methyl or acetyl; and x is 3.

28. The photoprotective composition as defined by claim 1, in which the water-soluble silicone comprising at least one terminal or pendent monovalent polyoxyalkylene group is present in concentrations ranging from 0.01% to 20% by weight relative to the total weight of the composition.

29. The photoprotective composition as defined by claim 1, further comprising at least one additional UV-A-active and/or UV-B-active organic or mineral screening agent, which is water-soluble, liposoluble or insoluble in the usual cosmetic solvents.

30. The photoprotective composition as defined by claim 29, comprising at least one additional organic screening agent selected from among anthranilates; cinnamic derivatives; dibenzoylmethane derivatives; salicylic derivatives; camphor derivatives; triazine derivatives; benzophenone derivatives; β,β-diphenylacrylate derivatives; benzotriazole derivatives; benzalmalonate derivatives; benzimidazole derivatives; imidazolines; bisbenzazolyl derivatives; p-aminobenzoic acid (PABA) derivatives; benzoxazole derivatives; methylenebis(hydroxyphenylbenzotriazole) derivatives; screening polymers and screening silicones; dimers derived from α-alkylstyrene; and 4,4-diarylbutadienes, and mixtures thereof.

31. The photoprotective composition as defined by claim 30, comprising at least one additional organic screening agent selected from among:

Ethylhexyl salicylate,

Ethylhexyl methoxycinnamate,

Octocrylene,

Butyl methoxydibenzoylmethane,

Phenylbenzimidazolesulfonic acid,

Benzophenone-3,

Benzophenone-4,

Benzophenone-5, n-Hexyl 2-(4-diethylamino-2-hydroxybenzoyl)benzoate,

4-Methylbenzylidenecamphor,

Terephthalylidenedicamphorsulfonic acid,

Disodium phenyldibenzimidazoletetrasulfonate, 2,4,6-Tris(diisobutyl 4'-aminobenzalmalonate)-s-triazine, Anisotriazine, Ethylhexyltriazone, Diethylhexylbutamidotriazone, Methylenebis(benzotriazolyl)tetramethylbutylphenol, Drometrizole trisiloxane, Polysilicone-15

1,1-Dicarboxy(2',2'-dimethylpropyl)-4,4-diphenylbutadiene, 2,4-bis[5-1(Dimethylpropyl)benzoxazol-2-yl(4-phenyl) imino]-6-(2-ethylhexyl)imino-1,3,5-triazine, and mixtures thereof.

32. The photoprotective composition as defined by claim 29, comprising at least one mineral screening agent selected from among coated or uncoated metal oxide pigments or nanopigments.

33. The photoprotective composition as defined by claim 32, in which the additional mineral screening agents are nanopigments of titanium oxide, amorphous or crystallized in rutile and/or anatase form, or of iron oxide, zinc oxide, zirconium oxide or cerium oxide.

34. The photoprotective composition as defined by claim 1, further comprising at least one agent for artificially tanning and/or browning the skin.

35. The photoprotective composition as defined by claim 1, further comprising at least one cosmetic adjuvant selected from among organic solvents, ionic or nonionic thickeners, softeners, humectants, opacifiers, stabilizers, emollients, silicones, insect repellents, fragrances, preserving agents, surfactants, fillers, pigments, polymers, propellants, acidifying or basifying agents or any other ingredient commonly employed in cosmetics and/or dermatology.

36. The photoprotective composition as defined by claim 1, formulated as a lotion or serum, an aqueous gel, an oil-in-water or water-in-oil emulsion; multiple emulsion, microemulsion, vesicular dispersion of ionic and/or non-ionic type or wax/aqueous phase dispersion.

37. The photoprotective composition as defined by claim 1, formulated as an oil-in-water or water-in-oil emulsion comprising not more than 1% by weight of emulsifying surfactant, relative to the total weight of the composition.

38. A method for photoprotecting the skin, lips and/or hair against the damaging effects of UV-radiation, comprising topically applying thereon a thus effective amount of a photoprotective composition comprising at least one aqueous phase and at least one system for screening out UV-radiation, further comprising:

(a) at least one partially or totally neutralized, crosslinked or non-crosslinked amphiphilic polymer of 2-acrylamidomethylpropanesulfonic acid (AMPS), and (b) at least one water-soluble silicone comprising at least one terminal or pendent monovalent polyoxyalkylene group.

* * * * *